(12) United States Patent
Freas et al.

(10) Patent No.: US 8,517,993 B2
(45) Date of Patent: Aug. 27, 2013

(54) COMPOSITE MR-COMPATIBLE STYLET

(75) Inventors: Mark Stephen Freas, Palm Bay, FL (US); Matthew S. Solar, Indialantic, FL (US)

(73) Assignee: Medtronic, Inc., Minneapolis, MN (US)

( * ) Notice: Subject to any disclaimer, the term of this patent is extended or adjusted under 35 U.S.C. 154(b) by 2218 days.

(21) Appl. No.: 11/278,492

(22) Filed: Apr. 3, 2006

(65) Prior Publication Data

US 2006/0235355 A1    Oct. 19, 2006

Related U.S. Application Data

(60) Provisional application No. 60/671,144, filed on Apr. 14, 2005.

(51) Int. Cl.
*A61M 5/178*    (2006.01)

(52) U.S. Cl.
USPC .................................................. 604/164.01

(58) Field of Classification Search
USPC ................. 604/1, 164.01–164.12; 600/412
See application file for complete search history.

(56) References Cited

U.S. PATENT DOCUMENTS

| 4,402,685 | A | * | 9/1983 | Buhler et al. | 604/523 |
| 4,498,902 | A | * | 2/1985 | Ash et al. | 604/164.05 |
| 5,006,122 | A | * | 4/1991 | Wyatt et al. | 606/130 |
| 5,545,176 | A | | 8/1996 | Murtfeldt | |
| 5,782,764 | A | | 7/1998 | Werne | |
| 2005/0234334 | A1 | | 10/2005 | Murphy et al. | |

FOREIGN PATENT DOCUMENTS

| EP | 127261 A1 | 12/1984 |
| EP | 1413251 A1 | 4/2004 |
| WO | WO 98/22022 | * 5/1998 |
| WO | WO-9822022 A1 | 5/1998 |

OTHER PUBLICATIONS

"International Search Report and Written Opinion for Application No. PCT/US2006/011996, date mailed Aug. 16, 2006", 11 Pages.

* cited by examiner

*Primary Examiner* — Nicholas Lucchesi
*Assistant Examiner* — Pritesh Patel
(74) *Attorney, Agent, or Firm* — Harness, Dickey & Pierce, PLC

(57) ABSTRACT

This document discusses, among other things, a stiffening stylet for use with a peel-away or other sheath. The stylet includes an MR-compatible ceramic core and an MR-compatible tubular covering, such as a polyester heat shrink tubing. The ceramic core and the tubular covering together provide a step to engage a stop feature of the sheath to inhibit overextension of the stylet beyond a distal end of the sheath.

20 Claims, 1 Drawing Sheet

COMPOSITE MR-COMPATIBLE STYLET

RELATED APPLICATION

This application claims the benefit of U.S. Provisional Application Ser. No. 60/671,144 filed Apr. 14, 2005, which is incorporated herein by reference.

TECHNICAL FIELD

This patent document pertains generally to medical instruments, and more particularly, but not by way of limitation, to an MR-compatible stylet.

BACKGROUND

In one example, image guided surgery (IGS) uses preoperative patient images to guide a subsequent medical procedure. The preoperative patient images are displayed on computerized IGS workstation. A surgical instrument is remotely tracked by an optical or other positioning system that is coupled to the IGS workstation. This permits an image of the instrument and/or its trajectory path to be displayed on the preoperative patient images, which, in turn, helps the surgeon plan the entry point and trajectory to a desired target location within the patient. In one example, the light emitting diodes (LEDs) or passive reflectors are attached to the surgical instrument. The optical positioning system includes a camera that can detect light from such locators to determine the position and orientation of the surgical instrument.

In another example, IGS uses intraoperative patient images to guide an ongoing medical procedure. In one such example, a trajectory guide is mounted to a patient's skull, which, in turn, is introduced into a magnetic resonance (MR) imaging apparatus. MR images obtained during the medical procedure are used to guide the procedure, which may involve adjusting the skull-mounted trajectory guide to obtain the desired trajectory toward a target in the patient's skull, and then inserting a medical instrument through a guide lumen of the trajectory guide, along the trajectory path, to the target location in the patient's skull. The present inventors have recognized, among other things, that when MR intraoperative imaging is being used to guide an ongoing medical procedure, the medical instruments being used in the procedure must be MR-compatible.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1:
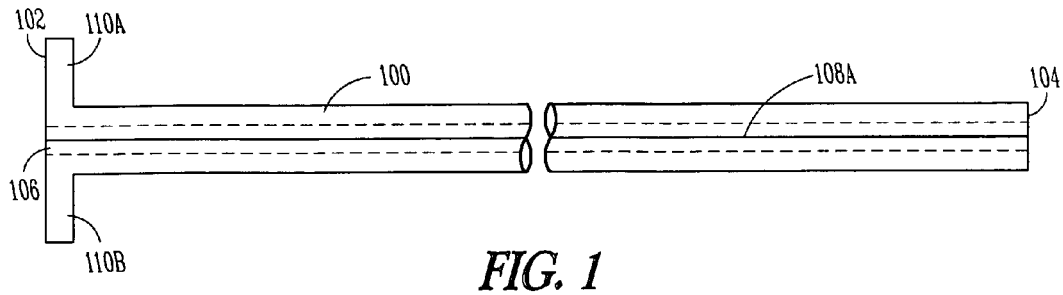
FIG. 1 is a side view showing one example of a plastic or other sheath or like medical device, such as a catheter.
Figure 2:
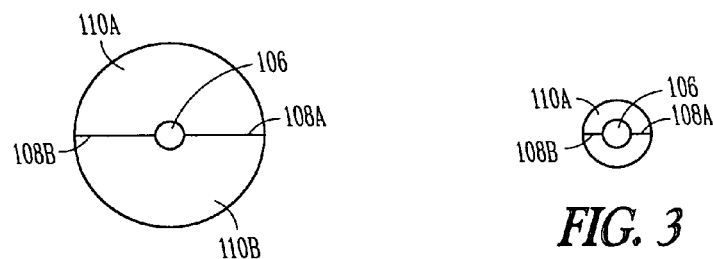
FIG. 2 is an end view of the proximal end of the sheath.
Figure 3:
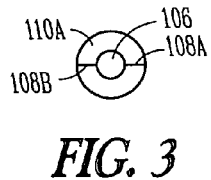
FIG. 3 is an end view of the distal end of the sheath.

FIG. 1 is a side view showing one example of a plastic or other sheath 100 or like medical device, such as a catheter. In this example, the elongate sheath 100 includes a proximal end 102 and a distal end 104. The distal end is typically introduced into a patient, for example, by inserting it through a patient-mounted or other trajectory guide or like device that provides an aimed trajectory toward a desired target in the patient. In one example, the trajectory guide is a NextFrame Model No. DB1021-MR skull-mounted instrument available from Image-Guided Neurologics, Inc. of Melbourne, Fla., U.S.A. A lumen 106 extends from the proximal end 102 to the distal end 104 of the sheath 100, permitting an medical instrument to be inserted through the sheath 100, if desired. In one example, the lumen 106 tapers inward slightly at the distal end 104, such as shown in FIG. 1, to provide a physical "stop" feature that inhibits further insertion of a medical device having a shoulder that butts against the stop. In the example of FIG. 1, the sheath 100 includes score-lines 108A-B on opposing sides, or similar features that allow the sheath 100 to be peeled-away into two separate portions by grasping and pulling apart corresponding handles 110A-B at the proximal end 102 of the sheath 100. This permits easy removal of the sheath 100 from within a lumen of a trajectory guide without affecting the positioning and placement of an instrument that has been inserted through the lumen 106 of the sheath 100 to a target. FIG. 2 is an end view of the proximal end 102 of the sheath 100. FIG. 3 is an end view of the distal end 104 of the sheath 100. In one example, the sheath 100 is a 4-French peel-apart sheath available as Item No. 7I1410 from B. Braun Medical, Inc. of Bethlehem, Pa., U.S.A.

Figure 4:
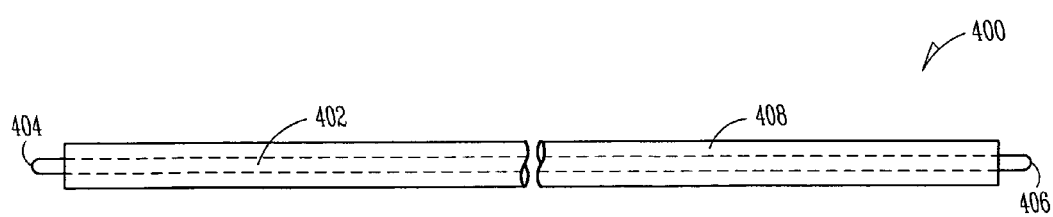
FIG. 4 shows an example of a stylet that includes an elongate cylindrical ceramic core, an intermediate portion of which is covered with an MR-compatible covering.

FIG. 4 is a side view showing a stylet 400. It is sometimes desirable to use an elongate stylet 400 during insertion of the sheath 100 into a patient. The stylet 400 is inserted into the lumen 106 of the sheath 100 before the sheath 100 is inserted into the patient. When so inserted, the stylet 400 provides stiffening to the sheath 100 to help provide easy and accurate insertion of the sheath 100 into the patient toward the target location. The stylet 400 also avoids coring tissue into the lumen 106, which might otherwise occur if the lumen 106 were left open during insertion of the sheath 100 into the patient. Avoiding such tissue coring is particularly important during insertion of the sheath 100 into brain tissue.

To be useful during a procedure that is being monitored using an MR imaging apparatus, the sheath 100 and stylet 400 should be MR-compatible. First, the sheath 100 and stylet 400 should be made from a material that is not influenced by the strong magnetic field of the MR-imaging apparatus. By contrast, an instrument made from a material influenced by the magnetic field of the MR-imaging apparatus could undergo unwanted displacement as the result of such magnetic fields. This reduces the accuracy of placing such an instrument, and can even pose a safety hazard that risks injury to the patient. The sheath 100 and stylet 400 should also be made of a material that does not produce an artifact on the resulting MR-image that distorts or obscures the MR-image, thereby reducing the image's diagnostic value to a physician.

For example, it is desirable that the stylet 400 should be made of a material that is stiffer than titanium, but which, unlike titanium, is MR-compatible in that it is not influenced by the magnetic field and does not produce a distortion artifact on the MR-image. The present inventors have recognized that a ceramic material can offer a suitable stiffness for the stylet 400. However, ceramic is brittle and may break—particularly if the diameter of a portion of the stylet 400 is reduced to provide a step, a shoulder, or a like stop-engaging feature to prevent over-insertion of the stylet beyond the distal end of the sheath 400, as illustrated FIG. 1.

Figure 5:
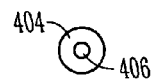
FIG. 5 is an end view of an example of the stylet 400, as viewed from either its proximal or distal end.

FIG. 4 shows an example of a stylet 400 that includes an elongate cylindrical ceramic core 402, which may include one or more beveled or rounded ends, such as its proximal end 404 and its distal end 406. In this example, an intermediate portion of the ceramic core 402 is coated or covered with a polymeric or other MR-compatible covering 408. In this example, the ceramic core 402 extends beyond the covering 408 at one or both of the ends 404 and 406, thereby providing a step or shoulder for engaging the stop at the distal end of the sheath 100. In one example, the covering 408 is a polymeric heat-shrink tubing such as used for angioplasty balloons, such as the 0.002 inch wall thickness polyester heat shrink sold as Item No. 090200CST by Advanced Polymers, Inc. of Salem, N.H., U.S.A., for example. The covering 408 provides the added benefit in that in inhibits breaking or shattering of the contained portion of the ceramic core 402. Moreover, even if the contained portion of the contained ceramic core 402 does break or shatter, the resulting pieces are advantageously retained within the covering 408. This provides an added measure of safety. In one example, the ceramic core is custom-machined to 0.060 inch diameter from alumina (ceramic) rod sold as Item No. AD-998 by Coorstek, Inc. of Golden, Colo., U.S.A., for example, the specifications for which are available at http://www.coorstek.com/materials/ceramics/alumina/ad998.asp, which is hereby incorporated by reference. In one example, the ceramic rod stock is machined to the desired diameter and then cut to approximately 10 inches in length to form the ceramic core 404 of the stylet 400. The ends of the ceramic core 404 are beveled into a semispherical shape. In one example, the covering 408 covers all but about 0.25 inches of each end of the ceramic core 404. FIG. 5 is an end view of an example of the stylet 400, as viewed from either its proximal or distal end.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, various features may be grouped together to streamline the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus the following claims are hereby incorporated into the Detailed Description, with each claim standing on its own as a separate embodiment.

What is claimed is:

1. A system comprising:
   a magnetic resonance (MR) compatible stylet, the stylet comprising:
      an MR-compatible elongate core;
      an MR-compatible covering encapsulating at least a portion of the core; and
      a step feature; and
   a sheath, sized and shaped to receive the stylet therein, wherein the sheath defines a lumen having a stop feature to engage the step feature of the stylet to limit movement of the stylet relative to the sheath, wherein the lumen is tapered inward to provide the stop feature.

2. The system of claim 1, in which the covering encapsulates a substantial portion of the core.

3. The system of claim 1, in which the covering includes a polymer covering.

4. The system of claim 1, in which the sheath is a peel-apart sheath.

5. The system of claim 1, further including a trajectory guide.

6. An invasive medical apparatus comprising:
   a sheath-like medical device defining a lumen having a distal end and a proximal end, wherein the lumen is wider adjacent the proximal end than the distal end;
   an MR-compatible core sized and shaped to be inserted into the lumen of the sheath-like medical device;
   a means for covering the core; and
   a means, associated with the core, for engaging the distal end of the sheath-like medical device to limit movement of the core and the means for covering the core relative to the sheath-like medical device.

7. The apparatus of claim 6, in which the sheath-like medical device is configured to be peeled apart.

8. The apparatus of claim 6, in which the MR-compatible core is made of ceramic.

9. The apparatus of claim 6, in which the means for covering the core include an MR-compatible material.

10. The apparatus of claim 9, in which the MR-compatible material includes a polymer covering.

11. The apparatus of claim 6, further including a trajectory guide.

12. The system of claim 2, wherein the covering includes a distal end and a proximal end, wherein the covering encapsulates the core between the distal end and the proximal end of the covering, wherein the core includes a proximal end that extends out of the proximal end of the covering, and wherein the core includes a distal end that extends out of the distal end of the covering, the proximal and distal ends of the core exposed from the covering.

13. The system of claim 1, wherein the sheath includes a distal end and a proximal end with a handle.

14. A system comprising:
   a magnetic resonance (MR) compatible stylet, the stylet comprising:
      an MR-compatible elongate core; and
      an MR-compatible covering encapsulating at least a portion of the core;
      a step feature; and
   a sheath, sized and shaped to receive the stylet therein, wherein the sheath includes a lumen having a stop feature to engage the step feature of the covering of the stylet to limit movement of the stylet relative to the sheath,
   wherein the sheath includes a distal end and a proximal end, wherein the lumen is wider adjacent the proximal end than the distal end, a width of the lumen adjacent the distal end sized so as to act as the stop feature for engaging the step feature.

15. The system of claim 4, wherein the sheath includes a score line along which the sheath can be peeled apart.

16. The system of claim 1, wherein the core is made at least partially out of a ceramic.

17. A system comprising:
   a magnetic resonance (MR) compatible stylet that includes:
      an MR-compatible elongate core having a distal end and a proximal end, the core being non-metallic;
      an MR-compatible covering that receives the core, and that is non-metallic, the covering including a distal end and a proximal end, the covering encapsulating the core between the distal end and the proximal end of the covering, the proximal and distal ends of the core extending out from the proximal and distal ends of the covering, respectfully, to be exposed from the covering; and
      a step feature;
   a sheath that receives the stylet therein, the sheath including:
      a distal end;
      a proximal end having a plurality of handles;
      a lumen that extends between the distal and proximal ends, the lumen being wider adjacent the proximal end as compared to the distal end, the lumen having a width adjacent the distal end to act as a stop for abutting and engaging the step feature and limiting movement of the stylet relative to the sheath; and
      at least one score line that extends longitudinally on the sheath, the at least one score line disposed between the plurality of handles, the sheath peelable into a plurality of portions along the score line; and
   a trajectory guide.

18. The system of claim 1, wherein the core and the covering are each non-metallic.

19. The system of claim 1, wherein the core and the covering cooperate to define the step feature.

20. The apparatus of claim 6, wherein the means for engaging the distal end includes a step feature, the core and the means for covering the core cooperating to define the step feature.

* * * * *